United States Patent
Moorman et al.

(10) Patent No.: US 10,161,835 B1
(45) Date of Patent: Dec. 25, 2018

(54) MICROSAMPLER AND METHOD OF MAKING THE SAME

(71) Applicant: National Technology & Engineering Solutions of Sandia, LLC, Albuquerque, NM (US)

(72) Inventors: Matthew W. Moorman, Albuquerque, NM (US); Ronald P. Manginell, Albuquerque, NM (US); Jerome A. Rejent, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 428 days.

(21) Appl. No.: 14/945,274

(22) Filed: Nov. 18, 2015

Related U.S. Application Data

(60) Provisional application No. 62/082,495, filed on Nov. 20, 2014.

(51) Int. Cl.
  *G01N 1/24* (2006.01)
  *G01N 1/14* (2006.01)
  *G01N 1/22* (2006.01)

(52) U.S. Cl.
  CPC ............ *G01N 1/14* (2013.01); *G01N 1/2273* (2013.01); *G01N 1/24* (2013.01); *G01N 2001/2282* (2013.01)

(58) Field of Classification Search
  CPC ..................... F16K 99/0032; G01N 1/14
  USPC ........................................... 73/863.11
  See application file for complete search history.

(56) References Cited

U.S. PATENT DOCUMENTS

| | | |
|---|---|---|
| RE32,309 E | 12/1986 | Hwang |
| 5,091,242 A | 2/1992 | Chung |
| 5,411,602 A | 5/1995 | Hayes |
| 5,439,639 A | 8/1995 | Vianco et al. |
| 5,820,922 A | 10/1998 | Ricco et al. |
| 5,830,389 A | 11/1998 | Capote et al. |
| 5,834,627 A | 11/1998 | Ricco et al. |
| 6,096,656 A | 8/2000 | Matzke et al. |
| 6,171,378 B1 | 1/2001 | Manginell et al. |
| 6,224,728 B1 | 5/2001 | Oborny et al. |
| 6,444,326 B1 | 9/2002 | Smith |
| 6,527,835 B1 | 3/2003 | Manginell et al. |
| 6,666,907 B1 | 12/2003 | Manginell et al. |
| 6,699,392 B1 | 3/2004 | Manginell et al. |
| 6,706,091 B1 | 3/2004 | Robinson et al. |
| 6,772,513 B1 | 8/2004 | Frye-Mason et al. |
| 6,786,716 B1 | 9/2004 | Gardner et al. |

(Continued)

FOREIGN PATENT DOCUMENTS

WO  WO 2009/045116 A1  4/2009

OTHER PUBLICATIONS

U.S. Appl. No. 14/332,831, filed Jul. 16, 2014, Moorman et al.
(Continued)

*Primary Examiner* — Walter L Lindsay, Jr.
*Assistant Examiner* — Philip Marcus T Fadul
(74) *Attorney, Agent, or Firm* — Helen S. Baca

(57) ABSTRACT

An aspect of the present disclosure relates to a microsampler for hermetically sealing a sample. In particular, such microsamplers can be useful for encapsulation of chemical, biological, and explosive samples for the purposes of archival sample storage. Methods of making and using such microsamplers are also described herein.

20 Claims, 5 Drawing Sheets

(56) References Cited

U.S. PATENT DOCUMENTS

| | | |
|---|---|---|
| 6,902,701 B1 | 6/2005 | Hughes et al. |
| 6,930,051 B1 | 8/2005 | Manginell et al. |
| 7,017,795 B2 | 3/2006 | Liu et al. |
| 7,022,266 B1 | 4/2006 | Craig |
| 7,059,512 B2 | 6/2006 | Arita et al. |
| 7,078,237 B1 | 7/2006 | Mowry et al. |
| 7,105,098 B1 | 9/2006 | Shul et al. |
| 7,118,712 B1 | 10/2006 | Manginell et al. |
| 7,168,298 B1 | 1/2007 | Manginell et al. |
| 7,399,449 B1 | 7/2008 | Oborny et al. |
| 7,422,724 B1 | 9/2008 | Manginell et al. |
| 7,597,014 B2 | 10/2009 | Tans |
| 7,708,943 B1 | 5/2010 | Robinson et al. |
| 7,727,314 B1 | 6/2010 | Manginell et al. |
| 7,799,280 B1 | 9/2010 | Manginell et al. |
| 7,847,406 B2 | 12/2010 | Arita et al. |
| 7,913,534 B1 | 3/2011 | Robinson et al. |
| 8,298,488 B1 | 10/2012 | Lewis et al. |
| 8,444,774 B2 | 5/2013 | Duschesne et al. |
| 8,736,000 B1 | 5/2014 | Manginell et al. |
| 9,472,689 B1 | 10/2016 | Elizondo-Decanini et al. |
| 2002/0143437 A1* | 10/2002 | Handique ........... B01F 13/0071 700/266 |
| 2004/0007275 A1* | 1/2004 | Hui Liu ............ B01L 3/502738 137/828 |
| 2004/0219732 A1* | 11/2004 | Burns ................. F16K 99/0015 438/200 |
| 2009/0035847 A1* | 2/2009 | Cho .................... B01F 11/0002 435/289.1 |
| 2015/0116939 A1* | 4/2015 | Bernstein ........... F16K 99/0042 361/699 |

OTHER PUBLICATIONS

U.S. Appl. No. 14/538,096, filed Nov. 11, 2014, Polsky et al.
U.S. Appl. No. 14/992,871, filed Jan. 11, 2016, Moorman et al.
U.S. Appl. No. 14/992,855, filed Jan. 11, 2016, Manginell et al.
U.S. Appl. No. 15/466,608, filed Mar. 22, 2017, Vianco et al.
U.S. Appl. No. 15/237,193, filed Aug. 15, 2016, Miller et al.
Achyuthan KE et al., "Design considerations for high-throughput screening and in vitro diagnostic assays," *Comb. Chem. High Throughput Screen.* Jul. 2007;10(6):399-412 (abstract, 1 p.).
Adamovics JA et al., "Gas Chromatography," Chapter 4 in *Chromatographic analysis of pharmaceuticals*, 2nd edition, Adamovics JA (ed.), 1997, Marcel Dekker, Inc., New York, NY, pp. 79-134.
Akutsu T et al., "Individual comparisons of the levels of (E)-3-methyl-2-hexenoic acid, an axillary odor-related compound, in Japanese," *Chem. Senses* May 2006;31:557-63.
Allardyce RA et al., "Detection of volatile metabolites produced by bacterial growth in blood culture media by selected ion flow tube mass spectrometry (SIFT-MS)," *J. Microbiol. Meth.* 2006;65:361-5.
Anderson G et al., "Determination of product shelf life and activation energy for five drugs of abuse," *Clin. Chem.* 1991;37(3):398-402.
Baker AK et al., "Analysis of non-methane hydrocarbons in air samples collected aboard the CARIBIC passenger aircraft," *Atmos. Meas. Tech.* 2010;3:311-21.
Bakwin PS et al., "Strategies for measurement of atmospheric column means of carbon dioxide from aircraft using discrete sampling," *J. Geophys. Res. Atmos.* 2003;108(D16):4514 (7 pp.).
Biet F et al., "Zoonotic aspects of *Mycobacterium bovis* and *Mycobacterium avium-intracellulare* complex (MAC)," *Vet. Res.* 2005;36:411-36.
Bostaris G et al., "Rapid detection methods for viable *Mycobacterium avium* subspecies *paratuberculosis* in milk and cheese," *Int. J. Food Microbiol.* 2010;141:S87-90.
Bunge M et al., "On-line monitoring of microbial volatile metabolites by proton transfer reaction-mass spectrometry," *Appl. Environ. Microbiol.* Apr. 2008;74(7):2179-86.
Chen H et al., "High-accuracy continuous airborne measurements of greenhouse gases ($CO_2$ and $CH_4$) using the cavity ring-down spectroscopy (CRDS) technique," *Atmos. Meas. Tech.* 2010;3:375-86.
Chen Z et al., "Thermally-actuated, phase change flow control for microfluidic systems," *Lab Chip* 2005;5:1277-85.
Crevoisier C et al., "Region US carbon sinks from three-dimensional atmospheric $CO_2$ sampling," *Proc. Nat'l Acad. Sci. USA* 2010;107(43):18348-53.
Daida JM et al., "A remote sensing unmanned aircraft vehicle system for flux measurements over forest canopies," *Proceedings of IEEE Topical Symposium on Combined Optical, Microwave, Earth and Atmosphere Sensing*, held on Mar. 22-25, 1994 in Albuquerque, NM, pp. 126-129.
Daida JM et al., "An unmanned aircraft vehicle system for boundary-layer flux measurements over forest canopies," International Geoscience and Remote Sensing Symposium (IGARSS '94)—Surface and Atmospheric Remote Sensing: Technologies, Data Analysis and Interpretation, held on Aug. 8-12, 1994 in Pasadena, CA, pp. 1248-1250.
De Maziere M et al., "Regional monitoring of tropospheric $NO_2$ and CO using remote sensing from high altitude platforms—preliminary concepts," Second International Workshop The Future of Remote Sensing, held on Oct. 17-18, 2006 in Antwerp, Belgium, 5 pp.
Dolch ME et al., "Volatile compound profiling for the identification of Gram-negative bacteria by ion-molecule reaction-mass spectrometry," *J. Appl. Microbiol.* 2012;113:1097-105.
Dubourg V et al., "The STRATEOLE project status: 200 pressurized balloons for the polar vortex study," *AIAA International Balloon Technology Conference*, held on Jun. 3-5, 19997 in San Francisco, CA, 7 pp.
Favela KH et al., "Microcollection of gases in a capillary tube: preservation of spatial and temporal resolution," *Anal. Chem.* 2012;84(19):8310-6.
Filipiak W et al., "Molecular analysis of volatile metabolites released specifically by *Staphylococcus aureus* and *Pseudomonas aeruginosa*," *BMC Microbiol.* 2012;12:113 (16 pp.).
Forsyth DS et al., "Detection of organotin, organomercury, and organolead compounds with a pulsed discharge detector (PDD)," *Anal. Bioanal. Chem.* 2002;374:344-7.
Galambos P et al., "Active MEMS valves for flow control in a high-pressure micro-gas-analyzer," *J. Microelectromech. Sys.* Oct. 2011;20(5):1150-62.
Gibson TD et al., "Not to be sniffed at," *Microbiol. Today* Feb. 2000;27:14-17.
Ginting D et al., "Construction and testing of a simple and economical soil greenhouse gas automatic sampler," *J. Plant Nutrition* 2007;30(9):1441-54.
Grob K et al., "Testing capillary gas chromatographic columns," *J. Chromatogr.* 1981;219:13-20.
Grob K, Jr. et al., "Comprehensive, standardized quality test for glass capillary columns," *J. Chromatogr.* 1978;156:1-20.
Harris NB et al., "Recovery of *Mycobacterium bovis* from soft fresh cheese originating in Mexico," *Appl. Environ. Microbiol.* Feb. 2007;73:1025-8.
Hesketh PJ et al., "Microvalve for fuel cells and miniature gas chromatographic system," *Sensors Update* 2007;13(1):233-302.
Jünger M et al., "Ion mobility spectrometry for microbial volatile organic compounds: A new identification tool for human pathogenic bacteria," *Appl. Microbiol. Biotechnol.* Mar. 2012;93(6):2603-14.
Karion A et al., "AirCore: an innovative atmospheric sampling system," *J. Atmos. Ocean Technol.* 2010;27:1839-53.
Kenisarin M et al., "Solar energy storage using phase change materials," *Renewable Sustainable Energy Rev.* 2007;11(9):1913-65.
Keppler F et al., "Methane emissions from terrestrial plants under aerobic conditions," *Nature* 2006;439:187-91.
Kukkonen CA et al., "Microsensors and microinstruments for space science and exploration," *Space Technol.* 1997;17(3-4):195-203.
Laurens JB et al., "Gas chromatographic analysis of trace gas impurities in tungsten hexafluoride," *J. Chromatogr. A* 2001;911:107-12.
Lewis PR et al., "Recent advancements in the gas-phase MicroChemLab," *IEEE Sensors J.* 2006;6(3):784-95.

(56) References Cited

OTHER PUBLICATIONS

MacDonald AE, "A global profiling system for improved weather and climate prediction," *Bull. Am. Meterol Soc.* 2005; 86:1747-64.
Machida T et al., "Worldwide measurements of atmospheric $CO_2$ and other trace gas species using commercial airlines," *J. Atmos, Oceanic Technol.* 2008;25:1744-54.
Mainelis G et al., "Performance characteristics of the aerosol collectors of the autonomous pathogen detection system (APDS)," *Aerosol Sci. Technol.* 2005;39:461-71.
Mäkiranta P et al., "Soil greenhouse gas emissions from afforested organic soil croplands and cutaway peatlands," *Boreal Env. Res.* 2007;12(2):159-75.
Manginell RP et al., "A materials investigation to enable miniaturized phase-change valving for greenhouse gas analysis with a micro analytical system," *Sandia Report No. SAND2010-6912*, 2010, 27 pp.
Manginell RP et al., "A monolithically-integrated µGC chemical sensor system," *Sensors* 2011;11:6517-32.
Manginell RP et al., "Diagnostic potential of the pulsed discharged helium ionization detector (PDHID) for pathogenic Mycobacterial volatile biomarkers," *J. Breath Res.* 2013;7:037107 (9 pp.).
Manginell RP et al., "Finite element modeling of a microhotplate for microfluidic applications," *Technical Proceedings of the 1999 International Conference on Modeling and Simulation of Microsystems*, held on Apr. 19-21, 1999 in San Juan, Puerto Rico, pp. 663-666.
Manginell RP et al., "Invited article: A materials investigation of a phase-change micro-valve for greenhouse gas collection and other potential applications," *Rev. Sci. Instrum.* 2012;83:031301 (11 pp.).
Manginell RP et al., "Mass-sensitive microfabricated chemical preconcentrator," *J. Microelectromech. Sys.* 2008;17(6):1396-407.
Marquis M et al., "Carbon crucible," *Science* 2008;320(5875):460-1.
McNerney R et al., "Production of volatile organic compounds by mycobacteria," *FEMS Microbiol. Lett.* 2012;328:150-6.
Moorman M et al., "Systems for plant volatile organic compound (VOC) analysis," *Sandia Report No. SAND2017-13451C*, 2017, 1 p.
Morimoto S et al., "A new compact cryogenic air sampler and its application in stratospheric greenhouse gas observation at Syowa Station, Antarctica," *J. Atmos. Ocean. Technol.* 2009;26:2182-91.
Nagel DJ, "Microsensor clusters," *Microelectron. J.* 2002;33(1-2):107-19.
Oh KW et al., "A review of microvalves," *J. Micromech. Microeng.* 2006;16(5):R13-R39.
Pal R et al., "Phase change microvalve for integrated devices," *Anal. Chem.* 2004;76(13):3740-8.
Pervov VS et al., "Supramolecular ensembles in eutectic alloys," *Russ. Chem. Rev.* 2003;72(9):759-68.
Pollmann J et al., "Evaluation of solid adsorbent materials for cryogen-free trapping—gas chromatographic analysis of atmospheric $C_2$—$C_6$ non-methane hydrocarbons," *J. Chromotogr. A* 2006;1134(1-2):1-15.
Pollmann J et al., "Sampling, storage, and analysis of $C_2$—$C_7$ non-methane hydrocarbons from the US National Oceanic and Atmospheric Administration Cooperative Air Sampling Network glass flasks," *J. Chromotogr. A* 2008;1188(2):75-87.
Roberge MT et al., "Evaluation of the pulsed discharge helium ionization detector for the analysis of hydrogen and methane in breath," *J. Chromotogr. A* 2004;1027:19-23.
Ross BM et al., "Stability of methylnicotinate in aqueous solution as utilized in the 'niacin patch test'," *BMC Res. Notes* Sep. 2008;1:89 (5 pp.).
Schuck TJ et al., "Greenhouse gas analysis of air samples collected onboard the CARIBIC passenger aircraft," *Atmos. Meas. Tech.* 2009;2:449-64.
Schulz K et al., "Tedlar bag sampling technique for vertical profiling of carbon dioxide through the atmospheric boundary layer with high precision and accuracy," *Environ. Sci. Technol.* 2004;38(13):3683-8.
Senecal AG et al., "Rapid detection of pathogenic bacteria by volatile organic compound (VOC) analysis," *Proc. SPIE* 2002;4575:121-31.
Shaikh KA et al., "Development of a latchable microvalve employing a low-melting-temperature metal alloy," *J. Microelectromech. Sys.* 2008;17(5):1195-203.
Sharma A et al., "Review on thermal energy storage with phase change materials and applications," *Renewable Sustainable Energy Rev.* 2009;13(2):318-45.
Sim WY et al., "A phase-change type micropump with aluminum flap valves," *J. Micromech. Microeng.* 2003;13:286-94.
Sonnenfroh D et al., "LED-based $CO_2$ sensor for balloon deployment," CLEO:2011—Laser Applications to Photonic Applications, OSA Technical Digest (CD) (Optical Society of America, 2011), paper CThT5 (2 pp.).
Spokas K et al., "Greenhouse gas production and emission from a forest nursery soil following fumigation with chloropicrin and methyl isothiocyanate," *Soil. Biol. Biochem.* 2005;37(3):475-85.
Spooner AD et al., "Evaluation of a combination of SIFT-MS and multivariate data analysis for the diagnosis of *Mycobacterium bovis* in wild badgers," *Analyst* 2009;134:1922-7.
Straus E et al., "Radioimmunoassay of tuberculoprotein derived from *Mycobacterium tuberculosis*," *Proc. Nat'l Acad. Sci. USA* Jul. 1980;77:4301-4.
Syhre M et al. "The scent of *Mycobacterium tuberculosis*," *Tuberculosis* 2008;88:317-23.
Syhre M et al., "The scent of *Mycobacterium tuberculosis*—Part II breath," *Tuberculosis* 2009;89:263-6.
Tans PP et al., "A feasible Global Carbon Cycle Observing System: a plan to decipher today's carbon cycle based on observations," *Global Change Biol.* 1996;2(3):309-18.
Tans PP et al., "Observational constraints on the global atmospheric $CO_2$ budget," *Science* 1990;247(4949):1431-8.
Terry SC et al., "A gas chromatographic air analyzer fabricated on a silicon wafer," *IEEE Trans. Electron Devices* 1979;26(12):1880-6.
Ubachs RLJM et al., "Microstructure evolution of tin-lead solder," *IEEE Trans. Components Packaging Technols.* 2004;27(4):635-42.
Weiss RF et al., "Quantifying greenhouse-gas emissions from atmospheric measurements: a critical reality check for climate legislation," *Philos. Trans. R. Soc. A* 2011;369:1925-42.
Whiting JJ et al., "High-speed two-dimensional gas chromatography using microfabricated GC columns combined with nanoelectromechanical mass sensors," *International Solid-State Sensors, Actuators and Microsystems Conference (Transducers 2009)*, held on Jun. 21-25, 2009 in Denver, CO, pp. 1666-1669.
Wilson ML, "General principles of specimen collection and transport," *Clin. Infect. Diseases* 1996;22:766-77.
Yang B et al., "A latchable microvalve using phase change of paraffin wax," *Sens. Actuat. A. Phys.* 2007;134(1):194-200.
Yang B et al., "A latchable phase-change microvalve with integrated heaters," *J. Microelectromech. Sys.* 2009;18(4):860-7.
Zhu J et al., "Fast detection of volatile organic compounds from bacterial cultures by secondary electrospray ionization-mass spectrometry," *J. Clin. Microbiol.* 2010;48:4426-31.

\* cited by examiner

MICROSAMPLER AND METHOD OF MAKING THE SAME

CROSS-REFERENCE TO RELATED APPLICATION

This application claims priority to U.S. Provisional Patent Application No. 62/082,495, filed on Nov. 20, 2014 under the title, "HERMETIC MICROSAMPLER FOR ARCHIVAL STORAGE," the entirety of which is incorporated herein by reference.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD

The present disclosure relate to a microsampler for hermetically sealing a sample (e.g., chemical, biological, and explosive samples). Methods of making and using such microsamplers are also described herein.

BACKGROUND

During a chemical, biological, or explosive (CBE) event, the presence of detection systems will help mitigate infrastructure damage and/or limit loss of life. Post-event analysis and/or attempts at confirmatory analysis will be complicated by the presence of decontamination substances, the rapid decay of CBE substances in the environment, and the presence of general environmental pollutants. This post-event analysis is important because it enables the gathering of technical intelligence, such as the specific type of CBE agent, its origin, the origin of its precursors, and the CBE deployment method. Additionally, a captured CBE sample could be analyzed at foreign or third party laboratories for the purposes of establishing political consensus about suspected CBE events. There is a need for simplified methods and platforms to capture CBE samples and optionally archive such samples for later analysis.

SUMMARY

Accordingly, certain aspects of the present disclosure relates to a phase-change microvalve technology in order to enable the development of safe, hermetic encapsulation of samples (e.g., aerosol samples, as well as chemical, biological, or explosive samples) for the purposes of archival sample storage. In the event that a portable (ground or UAV-mounted) or building-emplaced detection system positively detects a CBE event, this miniaturized archival storage system can be activated to entrain the CBE sample into an inert container and hermetically seal it within a miniaturized volume. This will allow subsequent confirmatory analyses to be performed on the sample at certified laboratory spaces for the purposes of agent attribution, technical intelligence gathering, and forensic documentation. Such analyses will provide policy makers, homeland security officials, and intelligence analysts with critical information about the event which could have important political and national security consequences.

In some non-limiting embodiments, the microsampler includes a normally-closed (NC) phase-change microvalve and a dual-layer stacked valve structure, thereby providing an archival storage system. In some embodiments, the NC valve operates in conjunction with a chamber maintained at vacuum pressure. When the phase-change material of the valve is thermally cycled and liquefied, the valve seal is ruptured, and the surrounding air rushes to fill the vacuum within the chamber. In other embodiments, the dual-layer stacked valve structure includes a normally-closed (NC) phase-change microvalve positioned at the entrance of the chamber, and a normally-opened (NO) phase-change microvalve positioned immediately below it. In some embodiments, the microsampler is deployed in conjunction with a detector configured to detect one or more CBE agents. Thus, in further embodiments, cycling of the NC valve is timed so that air containing the CBE sample will be drawn into the chamber as it leaves the detector. Once the volume within the chamber equilibrates, the NO valve can be cycled, and the CBE sample is hermetically sealed within the container. Additional details are described herein.

DEFINITIONS

As used herein, the term "about" means +/−10% of any recited value. As used herein, this term modifies any recited value, range of values, or endpoints of one or more ranges.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "microfluidic" or "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the application will be apparent from the following description and the claims.

BRIEF DESCRIPTION OF THE DRAWINGS

FIG. 4A shows an exemplary microsampler 400 with a baffle 440 structure.

FIG. 4B shows an exemplary assembly 450 including a microsampler 401 and a pumping system 402.

DETAILED DESCRIPTION

Certain aspects of the present disclosure relates to a microsampler having a microvalve technology. In general, the microvalve technology includes a phase-change material (PCM) that responds to heat and a heating element disposed in proximity to the PCM. To form a normally-closed (NC) valve, the PCM is configured to substantially block a seat opening on a valve seat. When the NC valve is actuated, the PCM unblocks the seat opening, thereby opening the valve. To form a normally-opened (NO) valve, the PCM is configured to be disposed around a valve orifice (e.g., an opening is formed within a bulk PCM or an annular ring of PCM is formed around an opening). When the NO valve is actuated, the PCM blocks the valve orifice, thereby closing the valve. Such valves can be configured in any useful manner, e.g., a dual-layer stacked valve structure, in order to form an actuating microsampler.

Figure 1:
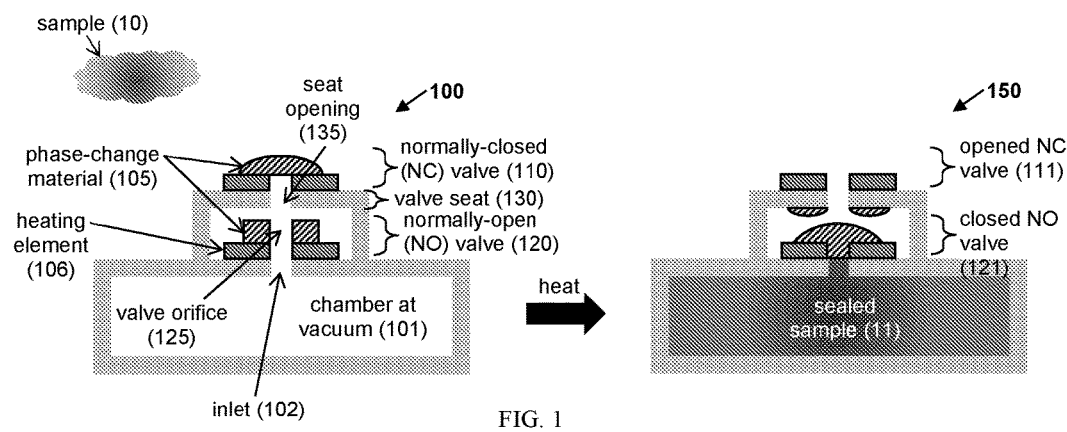
FIG. 1 is a schematic of an exemplary microsampler 100 with pump-free atmospheric intake capability due to an evacuated chamber 101.

FIG. 1 shows an exemplary architecture for a microsampler 100 including a stacked valve structure, which in turn includes an NC valve 110 disposed on a valve seat 130 and an NO valve 120 disposed below the valve seat 130. Each valve includes a PCM 105 and a heating element 106. According to one or more embodiments, the heating element 106 includes an opening, which is aligned with either the seat opening 135, the valve orifice 125, or the inlet 102. In some embodiments, the heating element is disposed in proximity to the PCM but not immediately beneath the PCM. In such embodiments, an opening in the heating element in not required.

The stacked valve structure includes a valve seat 130 disposed between the NC and NO valves 110, 120. As can be seen, the valve seat 130 includes a seat opening 135, and activating the NC valve 110 results in an opening that is formed in the opened NC valve 111 and aligned with the seat opening 135 and an opening in the heating element, according to at least one embodiment.

The NO valve 120 in turn includes a valve orifice 125, which is formed from an opening present in the PCM 105 and the heating element 106. The valve orifice 125 of the NO valve is aligned with inlet 102 of the chamber 101, which is optionally under vacuum, according to at least one embodiment. An exemplary NO valve is provided in FIG. 2.

Figure 3:
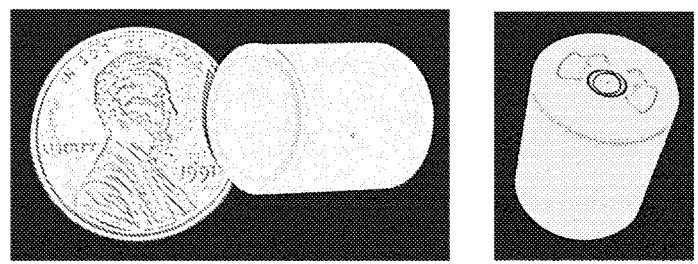
FIG. 3 is a drawing of (left) a completed microsampler chamber next to a U.S. penny and (right) an exemplary microsampler showing the heating element and valve seat metallization.

In order to capture a sample 10, both the NC and NO valves 110, 120 can be activated (e.g., by applying heat to the PCM). The valves can be activated in any order. In one instance, the NC valve 110 is opened, thereby providing a fluidic connection between the external environment and the internal chamber 101. As the chamber 101 is under vacuum, the pressure difference results in a capturing the sample 10 within the chamber 101. After sufficient time has elapsed to ensure capture of the desired sample, the NO valve 120 is closed, thereby providing a sealed sample 11. As can be seen, the sealed, activated microsampler 150 includes an opened NC valve 111 and a closed NO valve 121. FIG. 3 provides exemplary microsamplers having a circular cross-section for the chamber. Of course, the chamber can have any useful size (e.g., one or more microchambers) and geometry (e.g., having a circular, square, or rectangular cross-section).

Figure 4A:
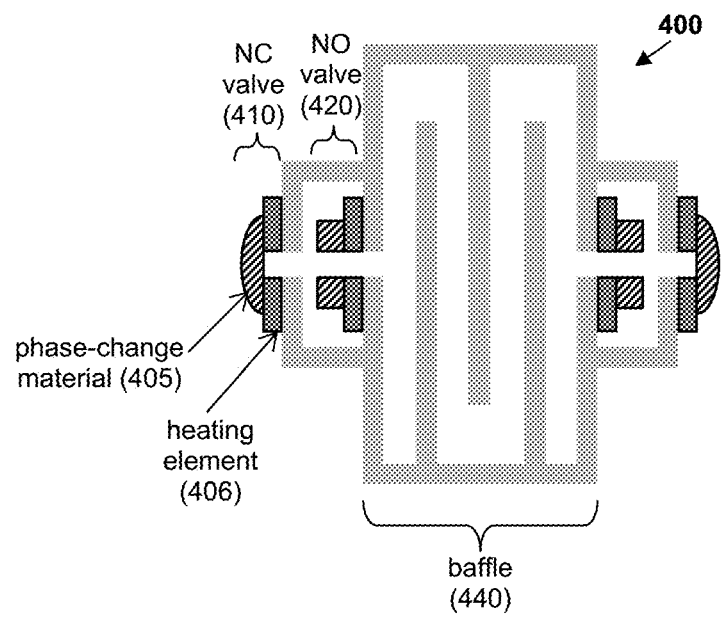
FIG. 4A-4B shows active environmental sampling capability from a microsampler 400, 450 with an internal tortuous path (baffle) to optimize aerosol collection.

The microsampler can include any useful internal structures. For instance, FIG. 4A shows an exemplary microsampler 400 having a dual-layer stacked valve structure disposed on two different sides of the chamber. Each stacked structure includes an NC valve 410 and an NO valve 420, which in turn include a PCM 405 and a heating element 406. As can also be seen, the chamber includes a baffle 440 structure, which provides an extended tortuous path. Such paths can be useful for guiding and/or condensing aerosol samples.

Furthermore, the microsampler can be integrated with any external component to form any useful system. For instance, FIG. 4B shows an exemplary system 450 including a microsampler 401 integrated with a pumping system 402, which in turn includes a port 404 and a pump 403. FIG. 5 shows a system 500 including a Peltier cooler 506 and heat sink 507 in order to electrically cool captured samples. The system 500 further includes a holder 505 adapted to mount the microsamplers 501, 502 to the cooler 506. Other useful components (e.g., any herein) can be employed with the microsamplers of the present disclosure.

The microsampler can also include arrays of valves, where such arrayed microsamplers can include a plurality of chambers, and a valve system associated with each chamber. Exemplary arrays are shown in FIGS. 7-9. In one non-limiting embodiment, the arrayed microsampler 700 includes a substrate 709 having a top layer 751 and a bottom layer 752.

The bottom layer 752 includes a plurality of chamber 701-704 configured to capture a sample or an analyte. In some embodiments, the top layer 751 includes a compartment 750, which is disposed above the chambers 701-704. Here, the compartment 750 is in fluidic communication with each of these chambers 701-704. This arrangement may be useful, for instance, when multiple aliquots of the same sample are desired and contamination is not a great concern.

Each chamber 701-704 is associated with a valve system. The valve system includes an NO valve 720 disposed in the bottom layer 752 and an NC valve 710 disposed in the top layer 751. Furthermore, each valve can be configured to be actuated individually. For instance, each valve can include an electrical connector 740 that is electrically connected to the heating element and an electrical contact 745. Each electrical contact 745 in turn can be readily accessible by a control unit to individually control each valve. As can be seen, electrical contacts can be arrayed on the edge(s) of the top and bottom layers 751, 752.

In an alternative configuration, the arrayed microsampler 800 can include a plurality of compartments 851-854 disposed above each internal chamber 801-804. In this architecture, contamination between each internal chamber is minimized because each chamber is only in fluidic communication with its own compartment. Again, the microsampler 800 can include a valve system 860 (e.g., an NC valve/NO valve combination) arranged between top and bottom layers, as well as electrical connectors 840 and electrical contacts 845 associated with each valve.

Figure 8:
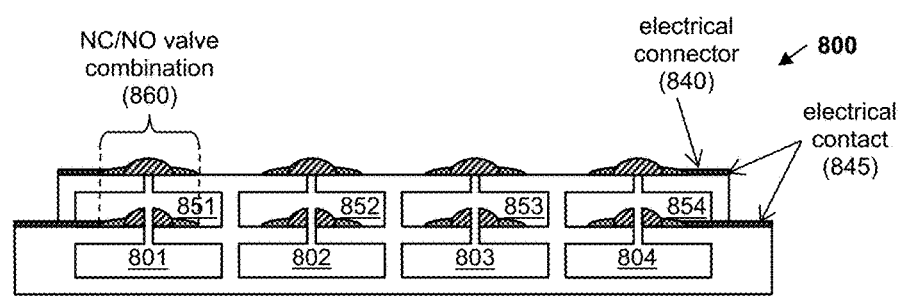
FIG. 8 is a schematic showing a cross-sectional view of an exemplary microsampler array 800.
Figure 9:
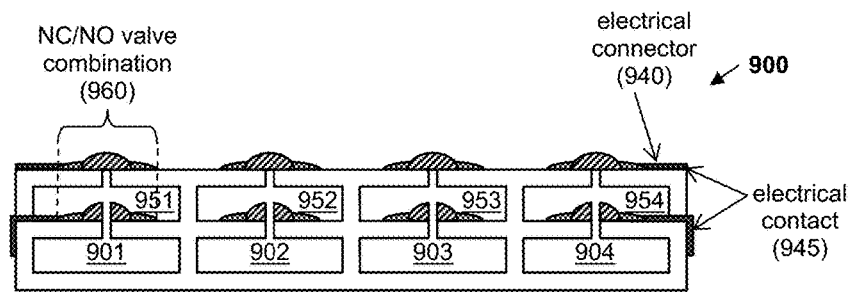
FIG. 9 is a schematic showing a cross-sectional view of another exemplary microsampler array 900.

Electrical connections can be accomplished with any useful arrangement. For instance, as seen in FIG. 8, the electrical contacts 845 are located on the top edges of each layer, where the top layer forms a smaller tier above the bottom layer. In another arrangement, the top and bottom layers can have similar dimensions, and the electrical connectors 940 and electrical contacts 945 can be located on the top edges and the sides of the array 900. The arrayed microsampler 900 can further include a plurality of compartments 951-954 disposed above each internal chamber 901-904, as well as a valve system 960 (e.g., an NC valve/NO valve combination) arranged between top and bottom layers.

Methods of Fabrication

The microsamplers of the present disclosure can be fabricated in any useful manner. In one instance, the chamber can be formed by cutting the ends of tubing. Then, plates can be affixed to the cut ends of the tubing (e.g., by brazing), thereby serving as end caps. Inlet(s) to the chamber can be drilled into one or more of the plates. Next, one or more metallization steps can be conducted to install heating elements and/or electrical connectors (e.g., heating traces) to the plates. Finally, a pre-molded PCM can be placed on or in proximity to the heating elements, thereby forming a PCM-based microvalve.

Figures 6A, 6B, 6C:
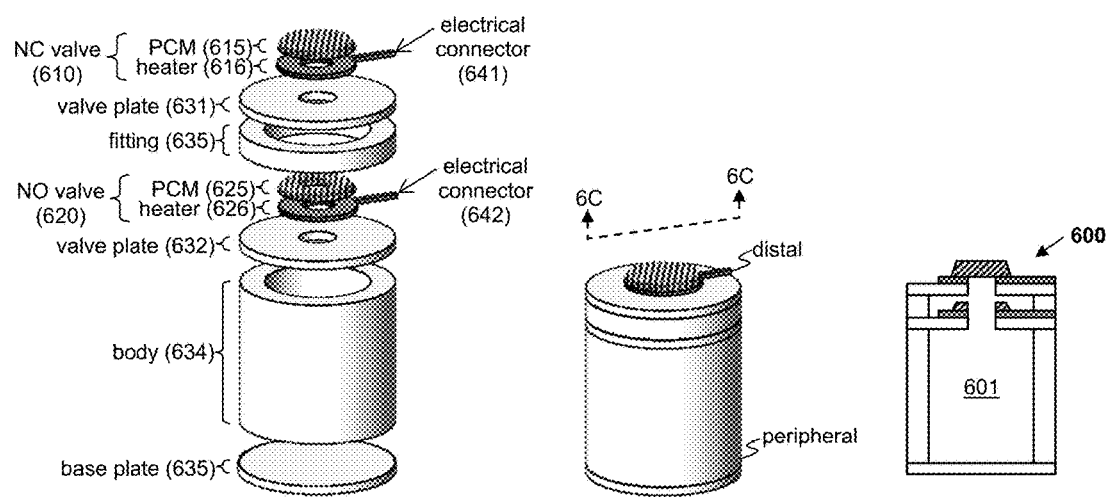
FIG. 6A shows schematics of an exemplary microsampler 600 in an exploded view.
FIG. 6B shows schematics of an exemplary microsampler 600 in a side view of the assembled microsampler.
FIG. 6C shows schematics of an exemplary microsampler 600 in a cross-sectional view along line 6C-6C.
Figure 7:
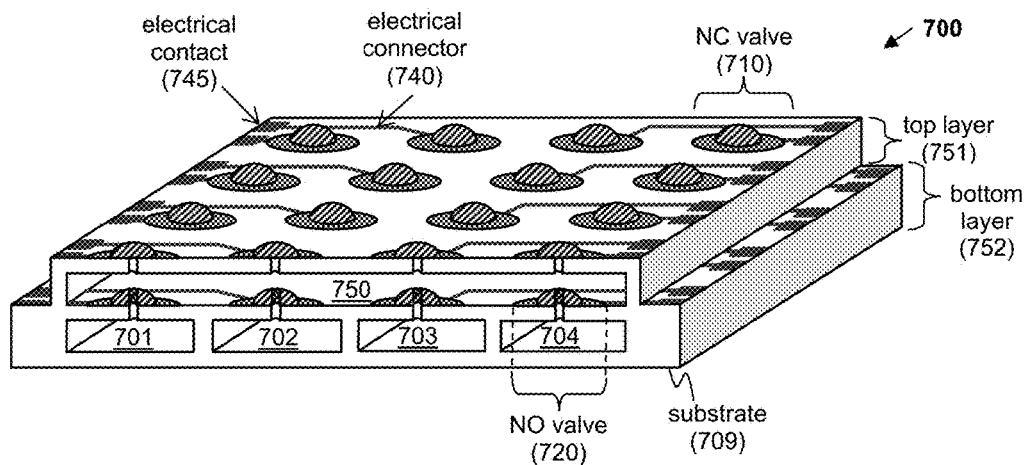
FIG. 7 is a schematic showing a perspective view of an exemplary microsampler array 700.

In another instance, each of the structures for the microsampler can be pre-formed, and then these structures can be assembled to form the completed microsampler. FIG. 6A-6C shows various exemplary structures for the microsampler. As can be seen, the microsampler 600 includes various components, including a body 634 having a distal end and a peripheral end. A base plate 635 is affixed to the peripheral end, and a valve plate 632 having an inlet is affixed to the distal end. To form the dual-stacked valve structure, the microsampler includes a fitting 635 disposed between the lower valve plate 632 and the upper valve plate 631. The NO valve 620 includes a heater 626 having an orifice and a PCM 625 disposed on the heater 626, where the PCM 625 is configured to ensure that the orifice is substantially blocked when the NO valve 620 is activated. The NC valve 610 includes a heater 616 having an orifice and a PCM 615 disposed on the heater 616, where the PCM 615 is configured to substantially block the orifice in the heater 616.

As can be seen, various inlets and orifices are aligned to ensure fluidic communication between the internal chamber 601 and the external environment when the NC valve 610 is actuated, in at least one embodiment. For instance, the orifice in the heaters 616, 626, the inlets or openings in the valve plates 631, 632, and the orifice in the PCM 625 for the NO valve are aligned and in fluidic communication with the chamber 601. FIG. 6B provides the integrated microsampler structure, and FIG. 6C provides the cross-sectional view along line 6C-6C showing the internal chamber 601 of the microsampler.

Figure 10:
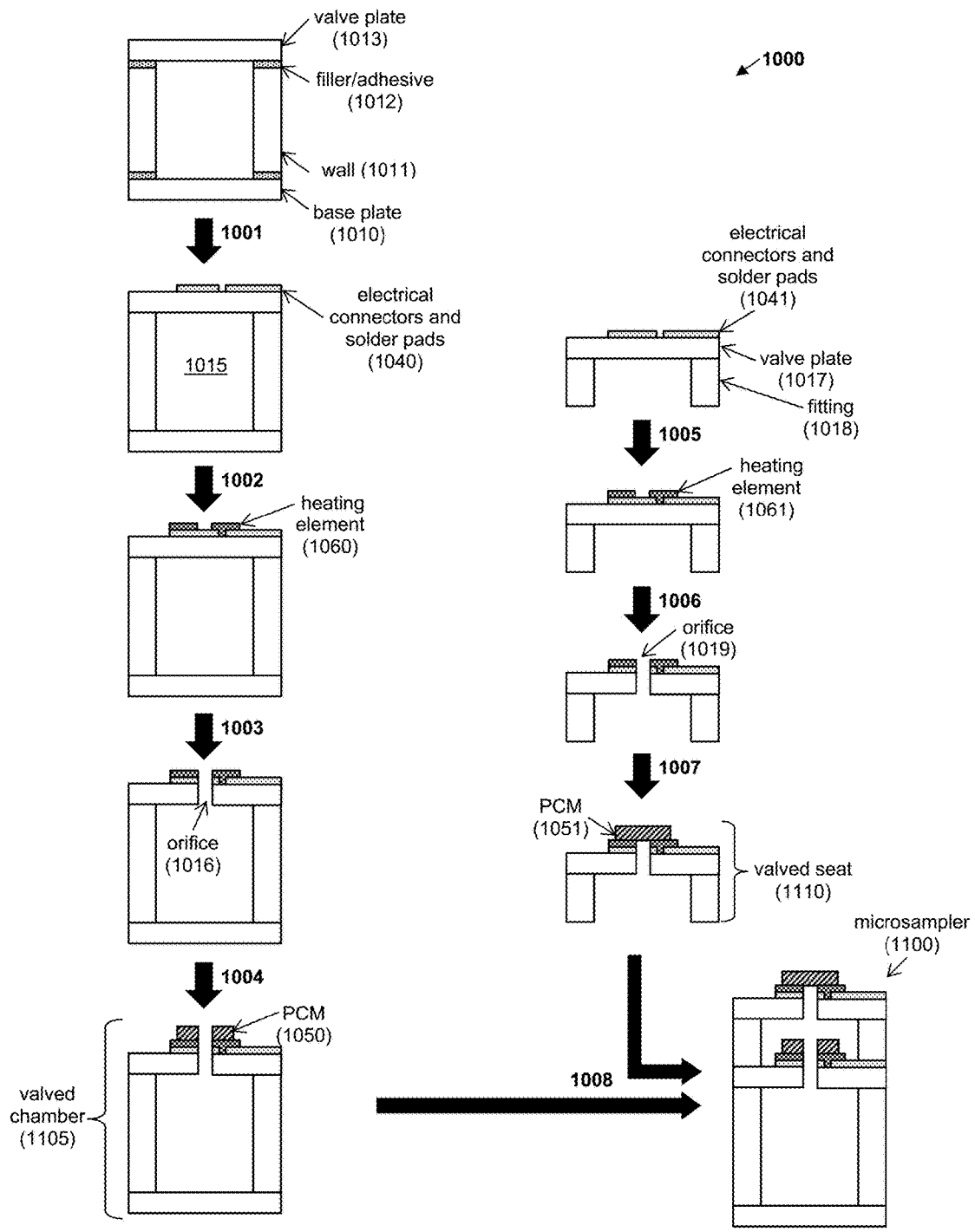
FIG. 10 is a schematic showing an exemplary method 1000 of fabricating a microsampler 1100.

In another instance (as shown in FIG. 10), the method 1000 can include forming two separate structures (e.g., a valved chamber 1105 and the valved seat 1110) that are then combined to form the final microsampler 1100.

The method 1000 can include providing a body having a valve plate 1013 and a base plate 1010 that are affixed to the walls 1011 of the body using a filler or adhesive 1012. In the metallization step 1001, the method includes providing one or more electrical connectors and/or solder pads 1040 on the valve plate 1013 surface above the internal chamber 1015. In the next metallization step 1002, a heating element 1060 is patterned such that it is electrically connected to the electrical connectors and/or solder pads 1040. In the drilling step 1003, an orifice 1016 is placed in the valve plate 1013. Alternatively, the drilling step 1003 can be performed prior to the metallization steps 1001, 1002; or the drilling step 1003 can be performed after the PCM deposition step 1004. To complete the valved chamber 1105, a PCM 1050 (e.g., a preformed PCM) is patterned, deposited, or aligned with the orifice 1016.

The valved seat can be formed in any useful manner. In one embodiment, the method 1000 includes providing a valve plate 1017 affixed to a fitting 1018, where electrical connectors and/or solder pads 1041 are disposed on the valve plate 1017. In a metallization step 1005, a heating element 1061 is patterned such that it is electrically connected to the electrical connectors and/or solder pads 1041. In the drilling step 1006, an orifice 1019 is placed in the valve plate 1017. Alternatively, the drilling step 1006 can be performed prior to the metallization step 1005; or the drilling step 1006 can be performed after the PCM deposition step 1007. To complete the valved seat 1110, a PCM 1051 (e.g., a preformed PCM) is patterned, deposited, or aligned with the orifice 1019. Finally, in an alignment step 1008, the valved seat 1110 is aligned with and affixed to the valved chamber 1105 to provide the microsampler 1100. Other methods for fabricating and testing such microsamplers are described herein, as well as in Manginell R P et al., "A monolithically-integrated μGC chemical sensor system," Sensors 2011; 11:6517-32; Manginell R P et al., "A materials investigation of a phase-change micro-valve for greenhouse gas collection and other potential applications," Rev. Sci. Instrum. 2012; 83:031301 (11 pp.); and Galambos P et al., "Active MEMS valves for flow control in a high-pressure micro-gas-analyzer," J. Microelectromech. Sys. 2011 October; 20(5):1150-62, each of which is incorporated herein by reference in its entirety.

Phase-Change Materials

As described herein, the microvalve includes use of one or more PCMs in conjunction with a heating element to melt the PCM. Any useful PCM can be employed, including those that have sufficient wettability that ensures adequate flow of the PCM to substantially block or unblock a valve orifice. Exemplary PCM include an organic material or an inorganic material. In particular embodiments, the PCM can be a eutectic, which is a composition of two or more components that melts or freezes nearly simultaneously. Eutectic metal alloys have a single melting point that is usually lower than the melting points of the corresponding two or more metals in the eutectic alloy. Exemplary eutectic metal alloys include a tin-lead alloy (e.g., a Sn—Pb alloy optionally including one or more other elements, such as $Sn_{63}Pb_{37}$, $Sn_{10}Pb_{90}$, $Sn_{62}Pb_{36}Ag_2$, $Sn_{62.5}Pb_{36}Ag_{2.5}$, $Sn_{97.5}Pb_1Ag_{1.5}$, $Pb_{90}Sn_5Ag_5$, $Pb_{97.5}Ag_{1.5}Sn_1$, $Sn_{51.2}Pb_{30.6}Cd_{18.2}$, $Sn_{62}Pb_{37}Cu_1$, $Sn_{70}Pb_{18}In_{12}$, and $Sn_{63}Pb_{37}P_{0.0015-0.04}$); an indium-silver alloy (e.g., an In—Ag alloy optionally including one or more other elements, such as $In_{97}Ag_3$, $In_{80}Ag_5Pb_{15}$); an indium-bismuth alloy (e.g., an In—Bi alloy optionally including one or more other elements, such as $In_{66.3}Bi_{33.7}$, $In_{61.7}Bi_{30.8}Cd_{7.5}$, and $In_{51.0}Bi_{32.5}Sn_{16.5}$ (Field's metal)); an indium-cadmium alloy (e.g., an In—Cd alloy optionally including one or more other elements, such as $In_{74}Cd_{26}$); an indium-lead alloy (e.g., an In—Pb alloy optionally including one or more other elements, such as $In_{80}Pb_{15}Ag_5$); a tin-silver alloy (e.g., an Sn—Ag alloy optionally including one or more other elements, such as $Sn_{96.5}Ag_{3.5}$, $Sn_{93.5}Ag_{3.5}Bi_{3.0}$, $Sn_{96}Ag_{2.5}Bi_{1.0}Cu_{0.5}$, $Sn_{88}Ag_{3.5}Bi_{4.5}In_{4.0}$, $Sn_{95.5}Ag_4Cu_{0.5}$, $Sn_{95.5}Ag_{3.9}Cu_{0.6}$, $Sn_{95.6}Ag_{3.5}Cu_{0.9}$, $Sn_{91.4}Ag_{4.1}Cu_{0.5}In_{4.0}$, and $Sn_{65}Ag_{25}Sb_{10}$); a bismuth-lead alloy (e.g., a Bi—Pb alloy optionally including one or more other elements, such as $Bi_{52}Pb_{32}Sn_{16}$, $Bi_{50}Pb_{26.7}Sn_{13.3}Cd_{10}$, $Bi_{49.5}Pb_{27.3}Sn_{13.1}Cd_{10.1}$ (Lipowitz Metal), $Bi_{50.0}Pb_{25.0}Sn_{12.5}Cd_{12.5}$ (Wood's metal), $Bi_{44.7}Pb_{22.6}In_{19.1}Cd_{5.3}Sn_{8.3}$, and $Bi_{49}Pb_{18}Sn_2In_{21}$); a gold alloy (e.g., an Au alloy optionally including one or more other elements, such as $Sn_{90}Au_{10}$, $Au_{80}Sn_{20}$, $Au_{96.8}Si_{3.2}$, $Au_{87.5}Ge_{12.5}$); a tin-copper alloy (e.g., a Sn—Cu alloy optionally including one or more other elements, such as $Sn_{99.3}Cu_{0.7}$ and $Sn_{95}Cu_{0.5}Ga_{0.5}In_4$); a tin alloy (e.g., a Sn alloy including one or more other elements, such as $Sn_{99.3}Cu_{0.7}$, $Sn_{91}Zn_9$, $Bi_{58}Sn_{42}$, $In_{52}Sn_{48}$, and $In_{58}Sn_{42}$); a zinc alloy (e.g., a Zn alloy including one or more elements, such as $Zn_{95}Al_5$, $Cd_{82.5}Zn_{17.5}$, and $Zn_{95}Sn_5$); and a lead alloy (e.g., a Pb alloy one or more elements, such as $Pb_{97.5}Ag_{2.5}$), where any of these alloys can optionally include a flux (e.g., an organic acid water-soluble flux, such as those including 2-propanol and glycerine (commercially available as Kester™ 2331-ZX soldering flux), or any including an acid and a solvent, such as those described in U.S. Pat. No. 8,444,774, which is incorporated herein by reference in its entirety) and any of these can be provided in any useful form (e.g., a paste, a wire, a mixture, etc.). Additional PCMs include solder-flux mixtures, such as those in U.S. Pat. Nos. 5,091,242, 5,411,602, 5,830,389, 7,017, 795, 7,022,266, 7,059,512, 7,847,406, and RE32,309, as well as any in Shaikh K A et al., "Development of a latchable microvalve employing a low-melting-temperature metal alloy," *J. Microelectromech. Sys.* 2008 October; 17(5):1195-203; and Yang B et al., "A latchable phase-change microvalve with integrated heaters," *J. Microelectromech. Sys.* 2009 August; 18(4):860-7, each of which is incorporated herein by reference in its entirety.

In other embodiments, the PCM is robust against environmental exposure and thermo-mechanically stable against temperature cycling. In some instances, organic and inorganic phase-change materials can lack rigorous hermetic sealing capabilities and robustness to aggressive chemical decontamination.

The PCM can be employed in any useful form to fabricate the microsampler. In one instance, the PCM is machined or cast to include an entrance hole concentric with the microsampler opening. In another instance, the PCM is patterned onto the microsampler. In yet another instance, the PCM is formed to substantially surround and not block an opening or orifice (thereby forming an NO valve), then the valve is actuated to form an NC valve.

Materials

The microsampler herein can be formed with any useful material. For instance, the electrodes can be formed from a conductive material, and the body or valve plates from an insulative material or an inert material. Exemplary materials include an insulative material, e.g., ceramic, alumina, ceria, polytetrafluoroethylene, or dielectric; a conductive material, e.g., a metal, stainless steel, steel, titanium, aluminum, copper, nickel, chromium, tungsten, or alloys thereof, as well as any substrate or material described in U.S. Pat. No. 6,444,326, which is incorporated herein by reference in its entirety; or an inert material, e.g., stainless steel. In particular embodiment, the surface of the material is passivated. For instance, passivation for stainless steel can include an amorphous silicon coating or a Siltek® coating, such as that described in U.S. Pat. No. 6,444,326, which is incorporated herein by reference in its entirety. In another embodiment, the surface of the material is coated with a biocompatible material, e.g., a cell medium (e.g., an agar medium), polyethylene glycol, etc. In other embodiments, the surface of the material can include one or more preservation agents, such as proteolytic inhibitors, lipolytic inhibitors, sugars, salts, electrolytes, etc.

Additional Components

The microsampler can be integrated or interfaces with one or more other components. For instance, a system can include a microsampler, or an array thereof, for use with a cooler (e.g., an active or passive cooling apparatus, which enables rapid cooling via a thermo-electric cooler in order to actively condense sample aerosols and/or minimize agent breakdown, such as those described in U.S. Pat. No. 6,706,091, which is incorporated herein by reference in its entirety); a sealing mechanism that is robust enough to undergo decontamination procedures and survive transport to certified laboratory spaces for subsequent gold standard confirmatory analyses on the samples (e.g., a seal having a helium leak rate below $1\times10^{-9}$ atm $cm^3/s$); one or more media (e.g., collection medium); a filter; an aerosol concentrator or collector; and/or a portable power source (e.g., to control one or more microvalves, or any other component).

Uses and Analytes

The microsamplers and systems herein can be employed for any useful purpose. The microsampler can capture any useful sample (e.g., an aerosol, such as a chemical aerosol or a bioaerosol (e.g., an aerosol including one or more viruses, bacteria, fungi, and/or odors, as well as any analyte described herein); a gaseous sample, such as a plume; or a liquid sample, such as an aqueous sample). The microsampler can be employed for hermetic storage, preservation, and/or retrieval. In one instance, the miniaturized archival storage system can include a microsampler that is configured to entrain a positive sample eluting from any useful sensor system.

In another instance, the microsampler can be employed to capture one or more analytes in a sample (e.g., a GC sample). Exemplary analytes include one or more of the following: light gases (e.g., hydrogen ($H_2$), methane ($CH_4$), carbon dioxide ($CO_2$), or carbon monoxide (CO), or any greenhouse gas (GHG)); volatile organic compounds (VOCs, e.g., from any source, such as microorganisms, pathogens, humans, toxic industrial chemicals (TICs), solvents, fixed/permanent gases, explosives, GHG, water contaminants, and/or chemical and biological warfare agents (CWAs and BWAs)), such as acids (e.g., isovaleric acid), aldehydes (e.g., acetaldehyde or 3-methylbutanal), ketones (e.g., acetoin or 2-nonanone), hydrocarbons (e.g., 2-butene or 1,10-undecadiene), alcohols (e.g., 2-methyl-1-propanol, 2-butanol), esters (e.g., ethyl formate or methyl 2-methylbutyrate), aromatics (e.g., benzene or toluene), including volatile nitrogen compounds (e.g., methylpyrrole), and volatile sulfur compounds (e.g., dimethylsulfide); semi-volatile organic compounds; human-specific volatile signals (e.g., hexenoic acid, such as 3-methyl-2-hexenoic acid or (E)-3-methyl-2-hexenoic acid; volatile signatures of pathogens (e.g., bacteria, fungi, food pathogens, or biological warfare agents, such as *Salmonella, Staphylococcus* (e.g., *S. aureus*), *Bacillus* (*B. anthracis*), Mycobacteria (e.g., *M. bovis* or *M. tuberculosis*), *Pseudomonas* (e.g., *P. aeruginosa*), *Neisseria* (e.g., *N. meningitidis*), *Streptococcus* (e.g., *S. pneumoniae*), *Klebsiella* (e.g., *K. oxytoca*), *Salmonella, Acinetobacter* (e.g., *A. baumannii*), *Enterobacter* (e.g., *E. cloacae*), *Penicillium* (e.g., *P. brevicompactum*), *Proteus* (e.g., *P. vulgaris*), *Serratia* (e.g., *S. marcescens*), *Yersinia* (e.g., *Y. pestis*), or *Escherichia* (e.g., *E. coli*)) and diseases in livestock and humans (e.g., acetaldehyde, acetic acid, acetone, acetonitrile, amine, 2-aminoacetophenone, butadiene, 1-butanol, 2-butanone, 1-decanol, dimethyl disulfide, dimethyl sulfide, ethanol, ethylene glycol, formaldehyde, hexanal, hydrogen sulfide, indole, isobutanol, isopentanol, 9-isopentanol, isopentyl acetate, isoprene, methanethiol, methanol, methyl p-anisate, 2-methyl-1-butanol, methyl nicotinate, 4-methylphenol, methyl phenylacetate, 2-nonanone, pentanol (including any isomer thereof), 2-pentanone, o-phenyl anisole, propanol, propene, pyrimidine, toluene, or trimethylamine); pesticides; water contaminants, e.g., trihalomethanes; explosives-related compounds (e.g., 2,3-butanediol, n-decane, dicyclohexylamine, 2,6-dimethylaniline, 2,6-dimethylphenol, 2,3-dimethyl-2,3-dinitrobutane (DMNB), 2-ethylhexanoic acid, methyl decanoate, methyl dodecanoate methyl undecanoate, nitrobenzene, 2-nitrotoluene, 3-nitrotoluene, nonanal, 1-octanol, triacetone triperoxide (TATP), or n-undecane); or chemical warfare agents (CWAs), e.g., dimethyl methylphosphonate (DMMP) in any sample (e.g., in soil, water, breath, saliva, food, liquid, milk, etc.), as well as gaseous or GC processed forms of any of these samples.

Other analytes and VOCs are described in Mainelis G et al., "Performance characteristics of the aerosol collectors of the Autonomous Pathogen Detection System (APDS)," *Aerosol Sci. Technol.* 2005; 39:461-71; Akutsu T et al., "Individual comparisons of the levels of (E)-3-methyl-2-hexenoic acid, an axillary odor-related compound, in Japanese," Chem. Senses 2006 May; 31:557-63; McNerney R et al., "Production of volatile organic compounds by mycobacteria," *FEMS Microbiol. Lett.* 2012; 328:150-6; Bostaris G et al., "Rapid detection methods for viable *Mycobacterium avium* subspecies paratuberculosis in milk and cheese," *Int. J. Food Microbiol.* 2010; 141:S87-90; Biet F et al., "Zoonotic aspects of *Mycobacterium bovis* and *Mycobacterium avium-intracellulare* complex (MAC)," *Vet. Res.* 2005; 36:411-36; Syhre M et al. "The scent of *Mycobacterium tuberculosis*," *Tuberculosis* 2008; 88:317-23; Syhre M et al., "The scent of *Mycobacterium tuberculosis*—Part II breath," *Tuberculosis* 2009; 89:263-6; Straus E et al., "Radioimmunoassay of tuberculoprotein derived from *Mycobacterium tuberculosis*," *Proc. Nat'l Acad. Sci. USA* 1980 July; 77:4301-4; Spooner A D et al., "Evaluation of a combination of SIFT-MS and multivariate data analysis for the diagnosis of *Mycobacterium bovis* in wild badgers," Analyst 2009; 134:1922-7; Harris N B et al., "Recovery of *Mycobacterium bovis* from soft fresh cheese originating in Mexico," *Appl. Environ. Microbiol.* 2007 February; 73:1025-8; Laurens J B et al., "Gas chromatographic analysis of trace gas impurities in tungsten hexafluoride," *J. Chromatogr. A* 2001; 911:107-12; Roberge M T et al., "Evaluation of the pulsed discharge helium ionization detector for the analysis of hydrogen and methane in breath," *J. Chromatogr. A* 2004; 1027:19-23; Forsyth D S et al., "Detection of organotin, organomercury, and organolead compounds with a pulsed discharge detector (PDD)," *Anal. Bioanal. Chem.* 2002; 374:344-7; Int. Pub. No. WO 2009/045116; Gibson T et al., "Not to be sniffed at," *Microbiol. Today* 2000 February; 27:14-17; Adamovics J A et al., "Gas Chromatography," Chapter 4 in *Chromatographic analysis of pharmaceuticals*, 2nd edition, Adamovics J A (ed.), 1997, Marcel Dekker, Inc., New York, N.Y., pp. 79-134; Ross B M et al., "Stability of methylnicotinate in aqueous solution as utilized in the 'niacin patch test'," *BMC Res. Notes* 2008 September; 1:89 (5 pp.); Achyuthan K E et al., "Design considerations for high-throughput screening and in vitro diagnostic assays," *Comb. Chem. High Throughput Screen.* 2007 July; 10(6):399-412; Ringer M et al., "Ion mobility spectrometry for microbial volatile organic compounds: A new identification tool for human pathogenic bacteria," *Appl. Microbiol. Biotechnol.* 2012 March; 93(6): 2603-14; Dolch M E et al., "Volatile compound profiling for the identification of Gram-negative bacteria by ion-molecule reaction-mass spectrometry," *J. Appl. Microbiol.* 2012; 113: 1097-105; Filipiak W et al., "Molecular analysis of volatile metabolites released specifically by *Staphylococcus aureus* and *Pseudomonas aeruginosa*," *BMC Microbiol.* 2012; 12:113 (16 pp.); Allardyce R A et al., "Detection of volatile metabolites produced by bacterial growth in blood culture media by selected ion flow tube mass spectrometry (SIFT-MS)," *J. Microbiol. Meth.* 2006; 65:361-5; Zhu J et al., "Fast detection of volatile organic compounds from bacterial cultures by secondary electrospray ionization-mass spectrometry," *J. Clin. Microbiol.* 2010; 48:4426-31; Bunge M et al., "On-line monitoring of microbial volatile metabolites by proton transfer reaction-mass spectrometry," *Appl. Environ. Microbiol.* 2008 April; 74(7):2179-86; Senecal A G et al., "Rapid detection of pathogenic bacteria by volatile organic compound (VOC) analysis," *Proc. SPIE* 2002; 4575:121-31; Grob K, Jr. et al., "Comprehensive, standardized quality test for glass capillary columns," *J. Chromatogr.* 1978; 156:1-20; Grob K et al., "Testing capillary gas chromatographic columns," *J. Chromatogr.* 1981; 219:13-20; and Manginell R P et al., "Diagnostic potential of the pulsed discharged helium ionization detector (PDHID) for pathogenic Mycobacterial volatile biomarkers," *J. Breath Res.* 2013; 7:037107 (9 pp.), each of which is incorporated herein by reference in its entirety.

EXAMPLES

Example 1: Microsampler Fabrication

An aspect of the present disclosure employs a microvalve technology. This microvalve includes a small opening (e.g., seat opening or valve orifice, such as about 250 μm in diameter), where the opening connects the interior chamber of the microsampler with the external environment.

Using our basic microvalve technology, two structures can be created: a normally-opened (NO) valve and a normally-closed (NC) valve. With these two valve structures as building blocks, we can create a large number of different sampling and capture schemes, as the subsequent size, shape, and material choice of the capture volume is largely independent of the valving mechanism. This technical attribute provides us with an immense flexibility in tailoring the microsampler to the desired sensing needs. The microvalve designs here are also appropriate for integration into liquid-based systems with active fluid control.

FIG. 1 (left) shows a microsampler design that uses an evacuated chamber 101 and a serial arrangement of an NC valve 110 and an NO valve 120 to produce an active air intake capability. When a sample 10 is needed, the NC microvalve 110 is thermally cycled, and the pressure difference between atmosphere and the evacuated chamber 101 creates a force that displaces the valve material of the NC valve 111 and pushes it through the microsampler seat opening to the inside of the valve seat 130 volume as shown in FIG. 1 (right). This opens the inlet 102 for sampler introduction. After the evacuated chamber 101 is filled by an incoming liquid or gas sample 10, the NO microvalve 121 is then cycled, sealing the volume. This microvalve design could be integrated with either a liquid or gas analysis system. This design also maintains the internal chamber in a pristine state prior to sample capture.

In one example, an annular resistive heating element 106 encircles the microsampler seat opening 135 or inlet 102, and over that a mass of phase-change material (PCM) 105 was deposited. Initially, we focused on Sn/Pb alloys as a candidate PCM. These alloys are not only inexpensive and common place but robust against environmental exposure and thermo-mechanically stable against temperature cycling. Some organic and inorganic phase-change materials may lack the rigorous hermetic sealing capabilities, as well as robustness to aggressive chemical decontamination.

Figure 2:
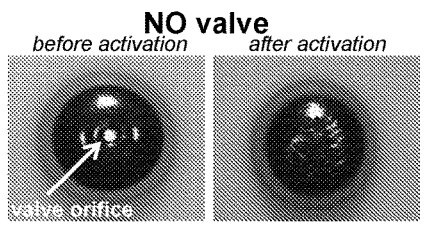
FIG. 2 shows photographs of a normally-opened (NO) valve before (left) and after (right) activation.

The Sn—Pb PCM was machined or cast to include a valve orifice concentric with the microsampler seat opening or inlet. A few watts of current were applied to the resistive heating element for several seconds to melt the phase-change material. Reflow of this material wetted the valve seat and hermetically sealed the valve orifice. FIG. 2 shows a mass of phase-change material, before and after actuation, wetted to a valve seat on an alumina substrate. As can be seen (FIG. 2, left), the fabricated mass of phase-change material includes a backlit opening, which is the valve orifice that aligns with an inlet in the alumina substrate. After actuating the NO valve (by applying current to the heating element or by thermal cycling), the mass of phase-change material collapsed and sealed the valve orifice (FIG. 2, right).

The microsampler fabrication process is highly versatile and capable of producing a variety of geometries and internal volumes as necessary. An exemplary microsampler was constructed from alumina (99.9% pure, 0.80 mm thick), which is a beneficial material for its relative strength, weight, ease of commercial purchase in a variety of shapes and sizes, and compatibility with a variety of fabrication processes including brazing and laser machining. Microsamplers can also be fabricated from commercial alumina tubing of a 2.30 mm diameter diced to the desired length to provide ~1 mL internal chamber (FIG. 3, left). Though it is easy to see how different lengths and diameters of tubes could be used to fabricate arbitrary sampler chambers smaller or larger than 1 mL. One mL was chosen as a representative size for a typical mass spectrometer analysis.

End caps (or plates) made from laser-machined alumina plate were then brazed on with commercial brazing foils. After assembly, the brazing was performed at high temperature in a vacuum oven, which assured a strong, hermetic seal between alumina parts. After brazing, a metallized pad was electron beam deposited through a shadow mask to form the valve metallization, which included the heating element deposited on the valve seat and a heating trace. This pad was a stack of Ti (100 nm thick), Ni (1 µm thick), and Au (5 µm thick). This metal could also be deposited using screen printing techniques. In the geometric center of the pad, a 0.25 mm diameter hole was laser drilled through both the metal pad and alumina substrate to create the valve orifice. FIG. 3 (right) shows a microsampler at this stage of assembly.

Preforms of the phase-change material (PCM) were punched from Sn/Pb eutectic solder that was rolled to a 0.38-0.51 mm thickness. To create an entrance hole in the final microvalve, sections of 0.20 mm diameter tungsten wire are used to cast the microvalve orifice. The Sn/Pb eutectic does not chemically bond with the tungsten wire, which means the wire can be easily removed once the preform is thermally-cycled. The PCM preform was placed over the metallization, and the tungsten wire was strung through the center orifice. The microsampler was thermally cycled using an external hotplate or oven (allowing many to be processed in parallel on industrial equipment such as a belt-furnace), which reflowed the eutectic solder and wetted the material onto the metallization pad. After cooling, the tungsten wire was removed, and the microsampler surface was cleaned of flux residue. The fabrication process detailed above represents the microsampler as currently realized. These basic structures have been produced and tested to demonstrate their ability to hermetically seal a gas sample within their volume without outgassing contaminants.

For applications that require an active atmospheric collection, such as when an unmanned aerial vehicle (UAV) is deploying a microsampler toward an agent plume or when a microsampler is mounted at a building air intake, we can integrate a microsampler with a miniature pump. In one embodiment, as seen in FIG. 4A, the microsampler 400 includes two sets of valves, where each set includes an NC valve 410 and an NO valve 420 in a serial arrangement. As can be seen, each valve includes a PCM 405 and a heating element 406. The microsampler also includes an internal chamber under vacuum. Optionally, the chamber can include a baffle 440 structure, allowing it to act as an impaction/condensation type collector to enhance aerosol droplet capture within the chamber. Alternatively, the chamber can be filled with a collection material configured to capture the desired agent within the sample. During sampling, the microsampler can operate as an impaction collector, which uses inertial change in order to guide the aerosol, and/or a condensation collector, which uses a sub-ambient temperature to condense moisture and aerosol. The NC microvalves and the evacuated chamber minimized environmental contamination during storage.

Figure 4B:
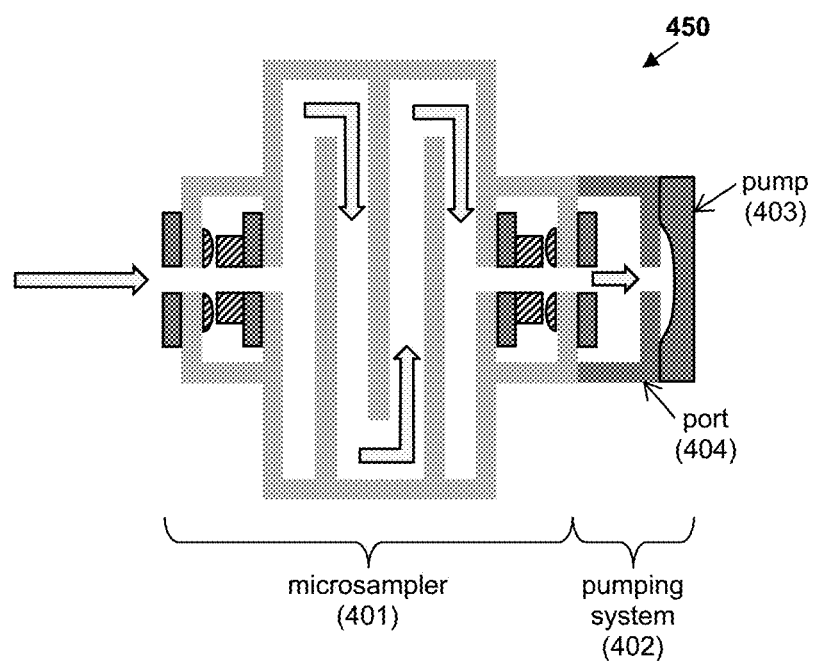

As shown in FIG. 4B, the microsampling system 450 can include a microsampler 401 for use with a pumping system 402, which in turn includes a pump 403 and a port 404 configured to interface the pump 403 with the microsampler 401. When an atmospheric sample is needed, the NC valves would thermally cycle, and an external pump 403 would draw air through the sampler 401. Once a sufficient amount of air had been drawn through the microsampler, the pump would shut off, and both NO valves would cycle and seal the volume. A skilled artisan would understand that other structural modification could be employed to capture the desired sample within the microsampler (e.g., use of one or more internal collection structures, one or more dual-stacked valves, etc.).

Example 2: Microsampler Modification for Bioaerosol Collection

To optimize the microsampler for bioaerosol collection, we propose a number of additions to the basic design herein. For instance, to promote the stability of the captured sample, we propose to deposit a bio-relevant coating within the chamber of the microsampler. An exemplary coating includes a thin layer of nutrient agar medium (such as Tryptic Soy Agar, TSA, for bacteria), as well as a cocktail of proteolytic and lipolytic inhibitors. The purpose of these last two components is to prevent sample degradation from environmental enzymes.

Figure 5:
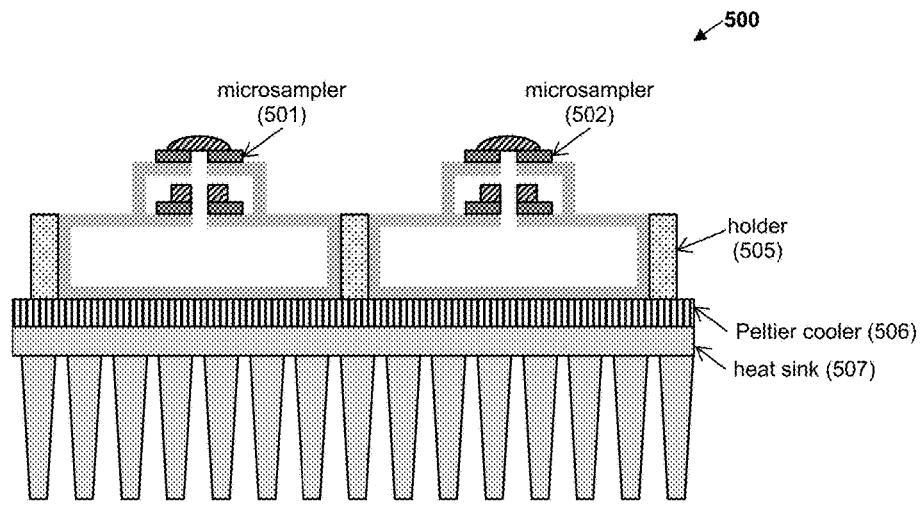
FIG. 5 is a schematic of an exemplary system 500 including microsamplers 501, 502 for use with a holder 505.

In addition, the microsampler can be configured to include a thermo-electric, or Peltier, cooling unit. A thermo-electric cooling unit will be integrated to reduce the temperature of the stored sample below ambient in order to promote bioaerosol condensation, minimize sample thermal degradation mechanisms, and encourage long-term sample preservation. A Peltier cooling unit is particularly beneficial due to its lack of moving parts, its high reliability, and its relatively small footprint and weight per unit of heat energy removed. Their primary drawback is the need for higher currents in order to maintain a large thermal gradient. It is our expectation that the relatively small thermal mass of the microsampler will allow for several hours of cooling at a modest cost in battery life. For situations where power is limited, lower-power thermo-electric cooling is critical. We estimate that two 1 mL microsamplers 501, 502 can be inserted into a machined aluminum holder 505 that is mounted to a thermo-electric cooler 506. FIG. 5 illustrates this configuration 500 mounted on a heat sink 507 for efficient heat removal. The thin aluminum holder would allow efficient heat removal from the microsampler walls, while providing a ready means for microsampler installation and replacement after use.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A microsampler comprising:
a chamber having a first inlet, wherein the chamber is under vacuum;
a first normally-opened (NO) valve comprising a first valve orifice in fluidic communication with the first inlet prior to activating the first NO valve, a first phase-change material disposed in proximity to the first valve orifice, and a first heating element disposed in proximity to the first phase-change material, wherein the first phase-change material substantially blocks the first valve orifice upon activating the first NO valve;
a first valve seat disposed above the first NO valve, wherein the first valve seat comprises a first seat opening; and
a first normally-closed (NC) valve disposed on the valve seat, wherein the first NC valve comprises a second phase-change material configured to substantially block the first seat opening prior to activating the first NC valve, and a second heating element disposed in proximity to the second phase-change material, wherein the second phase-change material substantially unblocks the first seat opening upon activating the first NC valve,
wherein the first NO valve is disposed between the chamber and the first NC valve.

2. The microsampler of claim 1, wherein the first phase-change material and the second phase-change material comprises a solder or a metal alloy.

3. The microsampler of claim 1, wherein activation of the first NO or NC valve comprises activating the first and/or second heating element, thereby heating the first and/or second phase-change material.

4. The microsampler of claim 3, further comprising a first electrical connector configured to contact electrically the first heating element and a second electrical connector configured to contact electrically the second heating element.

5. The microsampler of claim 1, wherein activating the first NO valve provides a hermetically sealed microsampler.

6. The microsampler of claim 1, wherein the first valve seat comprises a top surface and a bottom surface, the top surface supports the first NC valve, and wherein the bottom surface is treated to promote wetting of the second phase-change material.

7. The microsampler of claim 1, further comprising a cooler disposed beneath the chamber.

8. The microsampler of claim 7, further comprising a heat sink disposed beneath the cooler.

9. An array comprising a plurality of microsamplers of claim 1, wherein each microsampler is the same or different.

10. The array of claim 9, wherein each microsampler is located in a recessed portion of a holder.

11. The array of claim 9, wherein each chamber of each microsampler is defined in a substrate.

12. A microsampler comprising:
a chamber having a first inlet and a second inlet;
a first normally-opened (NO) valve comprising a first valve orifice in fluidic communication with the first inlet prior to activating the first NO valve, a first phase-change material disposed in proximity to the first valve orifice, and a first heating element disposed in proximity to the first phase-change material, wherein the first phase-change material substantially blocks the first valve orifice upon activating the first NO valve;
a first valve seat disposed above the first NO valve, wherein the first valve seat comprises a first seat opening;
a first normally-closed (NC) valve disposed on the valve seat, wherein the first NC valve comprises a second phase-change material configured to substantially block the first seat opening prior to activating the first NC valve, and a second heating element disposed in proximity to the second phase-change material, wherein the second phase-change material substantially unblocks the first seat opening upon activating the first NC valve;
a second NO valve comprising a second valve orifice in fluidic communication with the second inlet prior to activating the second NO valve, a third phase-change material disposed in proximity to the second valve orifice, and a third heating element disposed in proximity to the third phase-change material, wherein the third phase-change material substantially blocks the second valve orifice upon activating the second NO valve;
a second valve seat disposed above the second NO valve, wherein the second valve seat comprises a second seat opening; and
a second NC valve disposed on the second valve seat, wherein the second NC valve comprises a fourth phase-change material configured to substantially block the second seat opening prior to activating the second NC valve, and a fourth heating element disposed in proximity to the fourth phase-change material, wherein the fourth phase-change material substantially unblocks the second seat opening upon activating the second NC valve.

13. The microsampler of claim 12, wherein the chamber comprises one or more baffling structures.

14. The microsampler of claim 12, further comprising a pumping system in fluidic connection with the second inlet upon activating the second NC valve.

15. A method of fabricating a microsampler, the method comprising:

depositing one or more electrical connectors and/or solder pads on a valve plate disposed above a chamber;

forming a first heating element in electrical contact with the one or more electrical connectors and/or solder pads;

defining a valve orifice within the valve plate and in proximity to the heating element;

depositing a first phase-change material in proximity to the valve orifice and the heating element, thereby providing a valved chamber comprising a normally-opened (NO) valve; and attaching a valved seat to the valved chamber, wherein the valved seat comprises a normally-closed (NC) valve disposed on a valve seat and wherein the NO valve is disposed between the chamber and the NC valve.

16. The method of claim 15, wherein the depositing the first phase-change material comprises depositing a solder or a metal alloy in proximity to the valve orifice.

17. The method of claim 16, wherein the depositing the first phase-change material comprises forming an annular ring comprising the solder or metal alloy and aligning the valve orifice with a hole located within the annular ring.

18. The method of claim 15, wherein the valved chamber is provided in a bottom layer of a substrate.

19. The method of claim 15, wherein the attaching the valved seat to the valved chamber comprises disposing the valved seat in a top layer of a substrate.

20. A microsampler comprising:
a chamber having a first inlet, wherein the chamber is under vacuum;
a body having a distal end and a peripheral end, wherein the body defines the chamber;
a base plate affixed to the peripheral end of the body;
a lower valve plate affixed to the distal end of the body, wherein the first valve plate comprises the first inlet;
a first normally-opened (NO) valve disposed on the first valve plate, wherein the first NO valve comprises a first valve orifice in fluidic communication with the first inlet prior to activating the first NO valve, a first phase-change material disposed in proximity to the first valve orifice, and a first heating element disposed in proximity to the first phase-change material, wherein the first phase-change material substantially blocks the first valve orifice upon activating the first NO valve;
a first valve seat disposed above the first NO valve, wherein the first valve seat comprises an upper valve plate and a first seat opening disposed in the upper valve plate;
a fitting disposed between the lower valve plate and the upper valve plate; and
a first normally-closed (NC) valve disposed on the valve seat of the upper valve plate, wherein the first NC valve comprises a second phase-change material configured to substantially block the first seat opening prior to activating the first NC valve, and a second heating element disposed in proximity to the second phase-change material, wherein the second phase-change material substantially unblocks the first seat opening upon activating the first NC valve,
wherein the first NO valve is disposed between the chamber and the first NC valve.

* * * * *